United States Patent [19]

Kukes et al.

[11] 4,394,255
[45] Jul. 19, 1983

[54] ISOMERIZATION PROCESS

[75] Inventors: Semyon Kukes; Gerhard P. Nowack; Marvin M. Johnson, all of Bartlesville, Okla.

[73] Assignee: Phillips Petroleum Company, Bartlesville, Okla.

[21] Appl. No.: 395,940

[22] Filed: Jul. 7, 1982

[51] Int. Cl.$^3$ .............................................. C07B 5/23
[52] U.S. Cl. .................................... 585/667; 252/437
[58] Field of Search ...................... 585/667; 252/437; 208/134

[56] References Cited

U.S. PATENT DOCUMENTS

| | | | |
|---|---|---|---|
| 2,348,931 | 5/1944 | Schulze | 585/667 |
| 2,349,243 | 5/1944 | Bates | 196/52 |
| 2,387,994 | 10/1945 | Hillyer | 585/667 |
| 2,547,380 | 4/1951 | Fleck | 252/437 |
| 2,594,343 | 11/1942 | Pines | 585/667 |
| 2,854,498 | 9/1958 | Zimmerschied et al. | 208/134 |
| 2,921,081 | 1/1960 | Zimmerschied et al. | 252/437 |
| 2,960,551 | 11/1960 | Feller | 585/667 |
| 2,969,345 | 1/1961 | Coover et al. | 252/437 |
| 3,130,147 | 4/1964 | Dwyer et al. | 252/437 |
| 3,304,343 | 2/1967 | Mitsutani | 585/667 |
| 3,960,819 | 6/1976 | Jones et al. | 252/437 |

FOREIGN PATENT DOCUMENTS

| | | | |
|---|---|---|---|
| 55-13243 | 1/1980 | Japan | 252/437 |
| 56-140930 | 11/1981 | Japan | 252/437 |
| 761394 | 6/1967 | United Kingdom | 252/437 |

*Primary Examiner*—Delbert E. Gantz
*Assistant Examiner*—Cynthia A. Prezlock

[57] ABSTRACT

An aliphatic mono-olefin e.g. butene-2 is isomerized in the presence of a catalyst comprising zirconium phosphate and zirconium phosphate prepared from an aryl phosphonic acid to produce a corresponding terminal olefin selectively.

6 Claims, No Drawings

ISOMERIZATION PROCESS

The invention relates to the selective isomerization of an aliphatic mono-olefin. In accordance with another aspect, this invention relates to the selective isomerization of an aliphatic mono-olefin having an internal double bond to produce and to improve yield of the corresponding terminal olefin. A further aspect of this invention relates to a catalyst for isomerizing aliphatic mono-olefins.

BACKGROUND OF THE INVENTION

Terminal olefins, also called 1-olefins or alpha-olefins, are useful as reactants for a number of commercially important processes such as hydroformylation, sulfonation, alkylation and acid oligomerization. In these processes they are more reactive than internal olefins. The homologous series of 1-olefins can be prepared by the thermal cracking of paraffinic hydrocarbons. However, olefins produced by catalytic cracking will generally have close to thermodynamic equilibrium composition determined by the cracking temperature for the mixture of normal and branched isomers. These isomers are frequently not easily separated. When the normal and branched isomers can be separated from each other as with butenes, then the normal olefins can be treated by the catalyst of this invention to provide a fraction that is enriched in 1-olefins.

Accordingly, an object of this invention is to provide a process for the shifting of an internal double bond in an aliphatic mono-olefin hydrocarbon to the terminal position.

Another object of this invention is to provide a catalytic process for shifting an internal bond in an aliphatic mono-olefin to the 1- or the terminal position.

Another object of this invention is to provide a catalytic process for the selective isomerization or shifting of an internal unsaturation or double bond in an aliphatic mono-olefin to a terminal or 1-position.

Other aspects, objects as well as the several advantages of the invention are apparent from a study of this disclosure and the appended claims.

SUMMARY OF THE INVENTION

According to the present invention the double bond of an aliphatic mono-olefin is shifted from an internal position to a terminal position by contacting said mono-olefin under isomerization conditions with a catalyst essentially comprising zirconium phosphate and zirconium phosphonate which has been prepared from an aryl phosphonic acid and a compound of zirconium.

In accordance with one specific embodiment of the invention, the invention provides an isomerization process as described in which the catalyst used is prepared from aryl phosphonic acid and a compound of zirconium and used for the isomerization of mono-olefins having from 4 to 20 carbon atoms inclusive, to produce good yields of 1- or terminal double bond containing olefins.

In a preferred embodiment a feed stream containing $C_4$ hydrocarbons is treated with the invention catalyst for the production of butene-1 for example from butene-2.

DETAILED DESCRIPTION

The catalyst of this invention comprises zirconium phosphate and zirconium phosphonate prepared from an aryl phosphonic acid.

The catalyst is typically prepared by adding a solution of a soluble aryl phosphonic acid to a solution of a suitable zirconium compound. The resultant precipitate is filtered, washed and dried for 2-100 hrs. at 100°-200° C., although temperatures up to 350° C. may be employed. Where catalyst activation is carried out below 200° C., the use of inert atmosphere is optional. For catalyst activation at temperatures of 200°-350° C., the use of inert atmosphere, such as nitrogen, argon, or the like, is preferred.

Suitable aryl phosphonic acids are compounds of the following general formula:

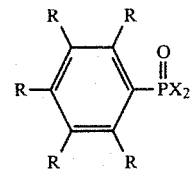

X can be a hydroxy group or a halide while the R groups can individually be H, alkyl, cycloalkyl, alkenyl, aryl, halo, nitro, cyano, sulfonato, and the like, and various combinations thereof. Exemplary compounds include 4-methylbenzene phosphonic acid, 3-chlorobenzene phosphonic acid, benzene phosphonic acid dichloride, and phenyl phosphonic acid, and the like. Mixtures can also be employed.

Compounds of zirconium which are applicable include the oxychlorides, halides, nitrates, sulfates, acetate, and the like, and mixtures thereof. Exemplary compounds include zirconyl chloride, zirconyl bromide, zirconyl iodide, zirconium tetrachloride, zirconium fluoride, zirconium nitrate, and the like.

The aryl phosphonic acid component and zirconium compound employed are dissolved in any suitable solvent. Suitable solvents include polar solvents such as alcohols, nitriles and water. Water is preferred.

Aliphatic mono-olefins having more than three carbon atoms are amenable to treatment by the catalyst of this invention. This includes branched chain as well as normal chain compounds. With both, the equilibrium concentration of the 1-olefin isomer increases with increasing temperature. In general, olefins being treated will have between 4 and 20 carbon atoms.

Such olefins include pentene-2, 2-methylbutene-2, hexene-2, hexene-3, 3-methylpentene-2, heptene-2, heptene-3, octene-2, octene-3, octene-4, and the like as well as mixtures thereof.

Especially preferred as feedstock to be treated with this catalyst are the isomeric n-butenes.

In carrying out the isomerization reaction with the catalyst of the invention suitable reaction conditions or isomerization conditions can be used which effectively cause double bond isomerization of the olefins in the feed. In general, the temperature at which isomerization is effected with this catalyst is about 300°-1100° F. Preferably the temperature will be in the range of about 500°-900° F. Reaction pressure can vary appreciably and can be subatmospheric and preferably will not exceed about 500 psig to avoid condensation reactions that ultimately lead to excessive coke formation on the catalyst.

Contact time of reactants on the catalyst expressed as liquid hourly space velocity (LHSV) can range between about 0.5 and 20. Preferably, LHSV will be between about 1 and 5.

EXAMPLE I

Inventive catalyst A was prepared by adding a solution of 58 g (0.367 moles) of phenylphosphonic acid, $C_6H_5P(O)(OH)_2$, dissolved in 600 mL of water to a solution of 58 g (~0.231 moles) of $ZrO(NO_3)_2 \cdot xH_2O$ in 600 mL of water. The precipitate was filtered, washed with hot water, and dried in an oven at 140° C. for 4 days. The catalyst contained by analysis 38.0 wt% Zr, 17.1 wt% P, had 64.5 m²/g surface area, and 0.294 mL/g pore volume.

Control catalyst B was prepared by adding a solution of 54.0 g (0.409 moles) of $(NH_4)_2HPO_4$ in 400 mL of water to a solution of 25 g (~0.100 moles) $ZrO(NO_3)_2 \cdot xH_2O$ dissolved in one liter of water. After being stirred for 5 minutes the precipitate was removed by filtration, washed with 1.5 L of hot water, dried in an oven, and finally calcined in air for 5 hours at 550° C. The catalyst contained by analysis 42.7 wt% Zr and 13.0 wt% P, had 141 m²/g surface area, and 0.437 mL/g pore volume.

EXAMPLE II

Runs were made using these catalysts to isomerize Phillips Pure Grade butene-2. Twenty-five mL portions of −14+45 mesh sieve fractions of catalysts were used. The catalyst was placed in a half-inch i.d. stainless steel reactor mounted vertically in a temperature controlled furnace; butene passed downflow at 2.0 LHSV, about 600° F., and at atmospheric pressure. Effluent from the reactor flowed through a glass trap at room temperature, then through a glass sampling container that could be closed and removed for GLC analysis. Butene-2 feed to the reactor was either dry or saturated with water vapor at room temperature to add about 3 mole% water vapor to it. This was done to see if the presence of water induced acid behavior in the catalyst. Table I presents some pertinent information about these runs and the results of the gaseous product analysis.

TABLE I

| Run | 1 | 2 | 3 | 4 | 5 | 6 | 7 | 8 | 9 | 10 | 11 | 12 |
|---|---|---|---|---|---|---|---|---|---|---|---|---|
| Catalyst | A | A | B | B | B | B | B | B | B | B | B | B |
| Water Added | No | Yes | No | No | No | No | No | Yes | Yes | Yes | Yes | Yes |
| Time on stream, Hr. | 0.7 | 1.3 | 0.5 | 1 | 2 | 3 | 5 | 0.5 | 1 | 2 | 3 | 5 |
| $CH_4$ | N.D. | N.D. | 0.005 | 0.004 | 0.003 | 0.001 | 0.002 | 0.005 | 0.003 | 0.002 | 0.003 | 0.002 |
| $C_2$'s | N.D. | N.D. | 0.02 | 0.01 | 0.01 | 0.003 | 0.006 | 0.02 | 0.01 | 0.01 | 0.01 | 0.006 |
| $C_3H_8$ | 0.001 | N.D. | N.D. | N.D. | N.D. | N.D. | N.D. | N.D. | N.D. | N.D. | N.D. | N.D. |
| $C_3H_6$ | 0.04 | 0.02 | 0.82 | 0.53 | 0.31 | 0.14 | 0.18 | 0.77 | 0.54 | 0.36 | 0.31 | 0.24 |
| $i\text{-}C_4H_{10}$ | N.D. | N.D. | 0.86 | 0.47 | 0.24 | 0.15 | 0.11 | 0.77 | 0.47 | 0.27 | 0.22 | 0.16 |
| $1\text{-}C_4H_8$ | 19.1 | 18.0 | 18.1 | 17.9 | 16.7 | 18.6 | 18.2 | 18.4 | 18.7 | 18.6 | 18.0 | |
| $n\text{-}C_4H_{10}$ | 0.30 | 0.29 | 0.98 | 0.76 | 0.57 | 0.50 | 0.46 | 0.97 | 0.78 | 0.61 | 0.56 | 0.50 |
| $i\text{-}C_4H_8$ | 0.65 | 0.44 | 2.78 | 2.14 | 1.54 | 1.19 | 1.08 | 2.51 | 1.92 | 1.44 | 1.26 | 1.07 |
| $c\text{-}2\text{-}C_4H_8$ | 30.7 | 31.0 | 28.1 | 28.5 | 28.5 | 29.9 | 29.6 | 27.9 | 29.0 | 29.7 | 29.8 | 29.1 |
| $t\text{-}2\text{-}C_4H_8$ | 47.5 | 47.9 | 43.2 | 43.9 | 44.0 | 44.5 | 45.4 | 42.7 | 44.8 | 46.1 | 46.3 | 44.8 |
| $C_4H_6$ | N.D. | N.D. | N.D. | N.D. | N.D. | N.D. | N.D. | N.D. | N.D. | N.D. | N.D. | N.D. |
| $C_5+$ | 1.89 | 1.27 | 5.21 | 5.55 | 6.99 | 6.85 | 4.55 | 6.09 | 4.09 | 2.80 | 2.91 | 6.15 |

During runs 37 and runs 8–12 about 12 mL of liquid product collected in the effluent trap. Analysis by GLC showed these liquid fractions to be about 60% $C_8$'s, about 25% lighter, and about 15% heavier, indicating that catalyst B was active to oligomerize butene. No measurable quantity of liquid product was obtained from catalyst A.

Table I shows that yields of propylene, isobutene, normal and isobutane, and $C_5+$ hydrocarbons were all substantially lower with inventive catalyst A than which control catalyst B. The presence of water vapor in the feed is not considered to have affected the activity or the selectivity of the catalysts.

We claim:

1. A process for the isomerization of an aliphatic mono-olefin hydrocarbon feed to shift the internal double bond therein to produce a corresponding terminal olefin which comprises subjecting said mono-olefin hydrocarbon under isomerization conditions to the action of a catalyst comprising zirconium phosphate and zirconium phosphonate wherein the catalyst used is prepared from an aryl phosphonic acid and a compound of zirconium.

2. A process according to claim 1 wherein said aryl phosphonic acid is phenylphosphonic acid.

3. A process according to claim 1 wherein the mono-olefin is at least one having from 4 to 20 inclusive carbon atoms.

4. A process according to claim 3 wherein the mono-olefins are inclusive of a substantial portion of butene-2.

5. A process according to claim 1 wherein the isomerization temperature is in the range of about 300°–1100° F.

6. A process according to claim 1 wherein the catalyst is prepared by combining a solution of phenylphosphonic acid with a solution of a zirconium salt followed by recovery of the precipitate and drying same.

* * * * *

Dedication 4,394,255.—*Semyon Kukes, Gerhard P. Nowack* and *Marvin M. Johnson,* Bartlesville, Okla. ISOMERIZATION PROCESS. Patent dated July 19, 1983. Dedication filed Oct. 23, 1984, by the assignee, *Phillips Petroleum Co.*

Hereby dedicates the entire remaining term of said patent to the Public.
[*Official Gazette December 11, 1984.*]